United States Patent
Weisemann et al.

(10) Patent No.: US 6,238,928 B1
(45) Date of Patent: May 29, 2001

(54) ANALYTICAL PROCESS FOR TESTING MIXTURES FOR TOXIC CONSTITUENTS

(75) Inventors: Claus Weisemann; Wolfgang Kreiss; Hans-Georg Rast, all of Bergisch Gladbach; Günther Eberz, Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 08/116,382

(22) Filed: Sep. 2, 1993

(30) Foreign Application Priority Data

Sep. 10, 1992 (DE) .................................. 42 30 264

(51) Int. Cl.[7] .............................. G01N 30/90; G01N 1/00
(52) U.S. Cl. ......................... 436/162; 436/172; 436/178; 422/70; 435/252.1; 210/198.3; 210/615; 210/658
(58) Field of Search ............................. 422/68.1, 69, 70; 436/178, 172, 161, 162; 435/252.1, 909; 210/658, 615, 198.3

(56) References Cited

U.S. PATENT DOCUMENTS 3,370,175 * 2/1968 Jordon et al. .................... 250/217
4,357,420 * 11/1982 Bostick et al. ....................... 435/8
4,581,335 * 4/1986 Baldwin ........................ 435/172.3
4,879,249 * 11/1989 Baldwin et al. ..................... 436/543

FOREIGN PATENT DOCUMENTS 0293775   12/1988   (EP) .
85/00890   2/1985   (WO) .
90/04037   4/1990   (WO) .

OTHER PUBLICATIONS

"Detection . . . Plates"; Bjurseth et al, Science, vol. 215 Jan. 1, 1982.*

* cited by examiner

Primary Examiner—Nina Bhat
(74) Attorney, Agent, or Firm—Norris McLaughlin & Marcus

(57) ABSTRACT

The mixture to be tested for toxic components is first separated into fractions by chromatography. The separated fractions are then contacted with luminescent microorganisms in the chromatographic system itself and the toxicity of the fractions is determined by measurement of the bioluminescence. The chromatographic separation may be carried out either by thin layer chromatography or by column liquid chromatography.

10 Claims, 2 Drawing Sheets

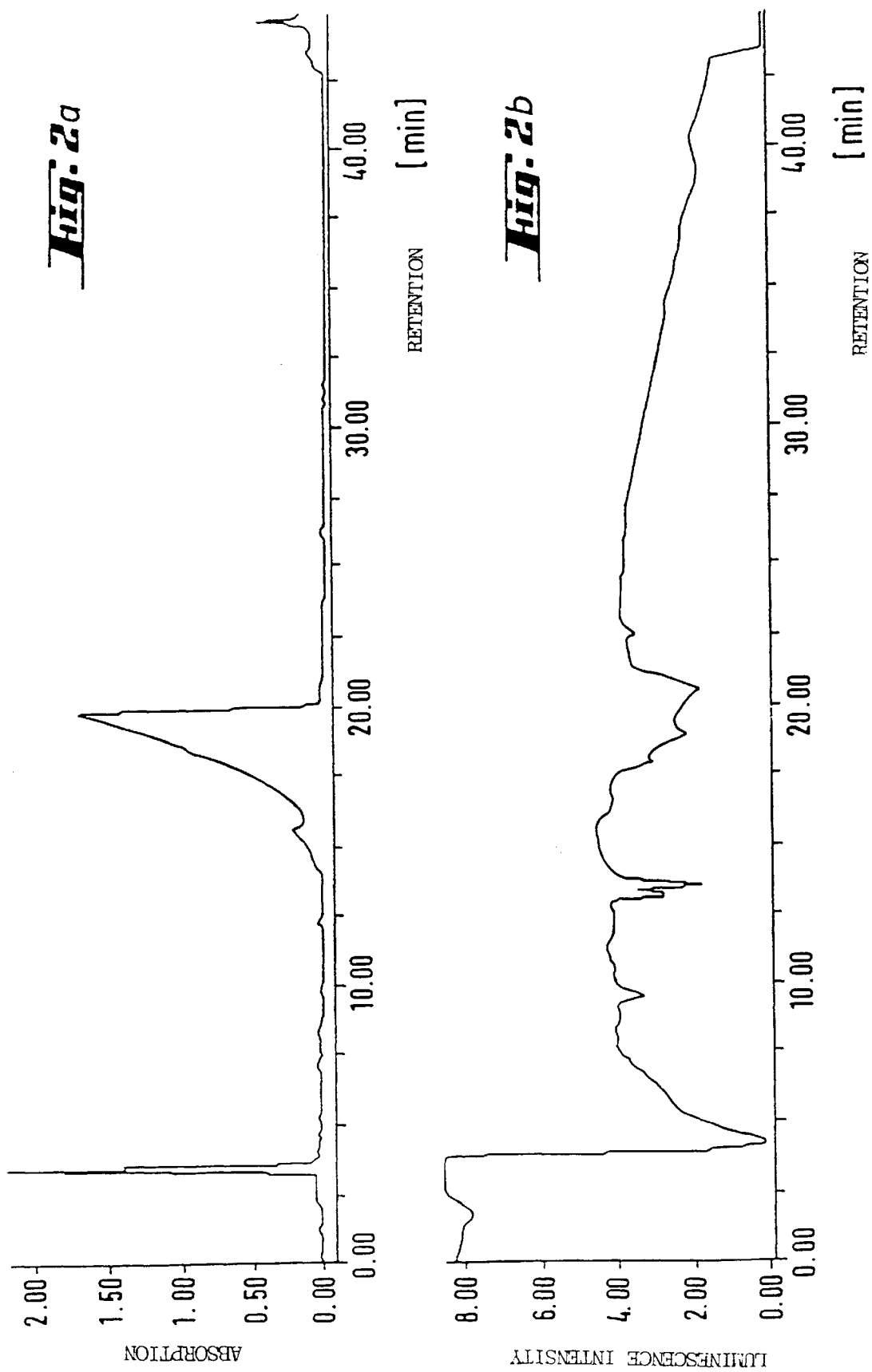

ANALYTICAL PROCESS FOR TESTING MIXTURES FOR TOXIC CONSTITUENTS

For many years, luminescent bacteria have been used in the toxicity testing of chemical compounds (see, for example, A. A. Bulich; G. Bitton, B. J. Dutkay, "Toxicity Testing Using Microorganisms", CRC Press, Boca-Raton, Fla., USA, pages 57 to 74). The principle of the luminescent bacteria test is based on substances toxic to bacteria leading to a reduction in the bioluminescence produced by the bacteria. This reduction is evaluated by measurement. In the case of a mixture of various chemical compounds, it has hitherto only been possible to evaluate the (integral) toxicity of the mixture as a whole. No information could be obtained as to the toxicity of the individual components involved.

Now, the problem addressed by the present invention was to provide a process for testing mixtures for toxic constituents based on the luminescent bacteria test which would enable the measured toxicities to be assigned to the individual components of the mixture. At the same time, the important boundary condition that the analytical process itself would not have any harmful effect on the luminescent bacteria would be satisfied.

According to the invention, the solution to this problem is characterized in that the mixture to be tested is first separated into fractions by chromatography, the separated fractions are contacted with luminescent microorganisms in the chromatographic system itself and the toxicity of the fractions is determined by measurement of the bioluminescence.

The fractions are advantageously separated by thin layer chromatography or column liquid chromatography. In the case of thin layer chromatography, the TLC plate is wetted with a suspension of luminescent microorganisms and the local bioluminescence assigned to the individual fractions is measured.

To this end, the TLC plate is advantageously contacted with a photographic film and the bioluminescence assigned to the individual fractions is evaluated on the exposed film either visually or by densitometry.

Where separation is carried out by column liquid chromatography, the suspension of luminescent microorganisms is continuously mixed with the eluate from the chromatographic column and the bioluminescence of the mixture is measured by means of a throughflow photometer.

The invention affords the following advantages:
1. Whereas conventional detection processes based on chromatography provide information on the identity, quantity and/or chemical structure of a mixture component, the process according to the invention provides direct information on the biological effect of a certain component of the mixture, i.e. the toxicity of a mixture can be directly assigned to discrete individual components of that mixture. The quality of the information obtainable by chromatographic separations is thus improved.
2. The selective detection of toxicity enables the effort and costs involved in the structural elucidation of unknown toxic compounds in mixtures to be considerably reduced because the work involved in structural elucidation (for example by isolation and subsequent spectroscopic examination) can be concentrated on those components of the mixture to which a toxic effect can be assigned on the basis of the toxicity detection results. Potential applications of this analytical process include the structural elucidation of unknown toxic components in wastewaters and the detection of biocides in various products.

The invention is illustrated by the following Examples in conjunction with the accompanying drawing.

Brief Description of the Drawings

FIGS. 2a and 2b graphically illustrates conventional HPLC chromatogram of a sample to be test for toxic components as well as the bioluminescent intensity of the sample.

Figure 1:
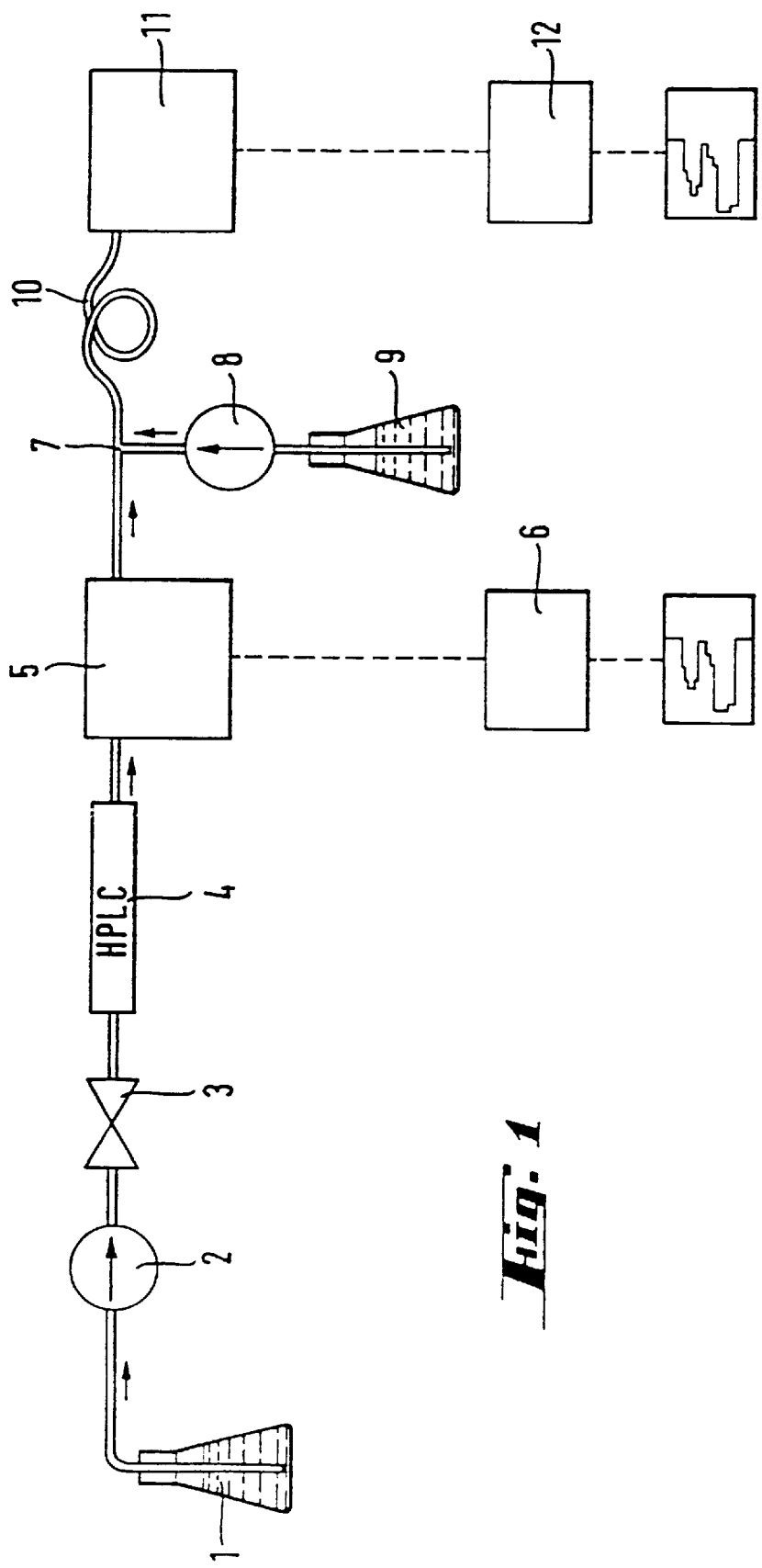
FIG. 1 illustrates an HPLC arrangement for toxicity detection.

1. Toxicity detection by thin layer chromatography

Toxicity detection by thin layer chromatography using luminescent microorganisms is carried out as follows:

The sample, for example an extract of a product to be tested for biocides, is separated by thin layer chromatography using standard laboratory methods. This may be followed by conventional detection by fluorescence extinction. After complete evaporation of the eluent, a suspension of luminescent microorganisms (in water containing 3% sodium chloride) is applied to the TLC plate by spraying or immersion in such a way that a thin film is left on the TLC plate. The plate is then covered with a transparent film or with a glass plate. A photographic film is then placed on this glass plate in a dark room and left for 0.5 to 15 minutes. The film is then developed and fixed by standard laboratory methods. Toxic fractions on the TLC plate may then be assigned to unexposed or under exposed parts of the film.

Example

| | |
|---|---|
| Sample: | Extract of a product to be tested for biocides |
| Solvent: | Methanol/isopropanol/water (1/1/1 parts by volume) |
| TLC plate: | Kiesegel (silica gel) 60 with Fluoreszenzindikator (fluorescence indicator) $F_{252}$, products of Merck, Darmstadt, Art. No. 5715. Before separation, the TLC plate is washed twice with methanol and then dried. |
| Eluent: | n-Heptane/dichloromethane/methanol (15/4/1 parts by volume). Development is carried out vertically in a simple TLC chamber |
| Luminescent microorganisms: | *Photobacterium phosphoreum* |
| Film: | Agfa Scopix Video 5B |
| Exposure time: | 14 mins. |

2. High-pressure liquid chromatography (HPLC)

An HPLC arrangement for toxicity detection is diagrammatically illustrated in FIG. 1. The eluent is introduced into the chromatographic column 4 from the storage vessel 1 by the HPLC pump 2 via the sample input valve 3. The fractions (eluate) issuing successively from the column 4 are evaluated in the usual way with a UV detector 5 in an adjoining evaluation unit 6. A throughflow cell is used as the measuring cell in the UV detector 5. A suspension of luminescent microorganisms is then continuously introduced from the storage vessel 9 into the eluate stream issuing from the throughflow cell by the metering pump 8 via a tee 7. The eluate and the suspension of luminescent bacteria are thoroughly mixed in the mixing compartment 10. The mixture is then delivered to a throughflow photometer 11 in which the bioluminescence of the individual fractions is measured and evaluated (evaluation unit 12).

Example

| | |
|---|---|
| Sample: | Aqueous sample to be tested for toxic components |
| High pressure liquid chromatograph: | Hewlett-Packard HP 1050 with auto-sampler and MWD detector |

-continued

| Example | |
|---|---|
| Pump for delivering the bacterial suspension: | Biotronik BT 8100 |
| Data evaluation: | GINA Software (Ravtest) |
| HPLC column: | Shandon Hypersil ODS, 5 μm; 10 cm × 0.4 cm diameter |
| Mixing coil: | Biorad biocompatible after-column derivatization system |
| Throughflow photometer: | Ravtest Ramona 90 |
| Sample volume: | 20 μl (sample loop) |
| Eluent: | Water containing 3% NaCl; 1.5 ml/min. |
| Flow rate of luminescent bacteria: | 1 ml/min. |
| Detection wavelength: | (UV detection): 220 nm |
| Bacteria: | Photobacterium containing 3% NaCl, cooled to 0° C. |

The recorded results are shown in FIGS. 2a and 2b. The upper curve shows a conventional HPLC chromatogram of a sample to be tested for toxic components as measured with the UV detector 5 and the evaluation unit 6. The lower curve shows the bioluminescence of the same eluate as measured with the throughflow photometer 11 and the evaluation unit 12.

A UV-active main component can be seen at a retention time of approx. 20 mins. together with a secondary component at a retention time of approx. 15 mins.

In the toxicity detection, there are three groups of signals, namely: a small signal at approx. 10 mins., a double signal at approx. 14 mins. and the signal belonging to the main component at approx. 20 mins.

Interestingly, the first two groups of signals do not correspond with the throughflow-photometric detection. The components of the tested mixture causing these signals obviously cannot be detected by UV detection at 254 nm and/or are not present in a sufficient concentration for this purpose.

However, the luminescence attenuation at approx. 10 mins. and at approx. 14 mins. shows that toxic components are eluted at these retention times.

To indicate the level of toxicity, a defined quantity of a substance of known toxicity may be chromatographed under identical conditions with an identical bacterial suspension and with a minimal time difference in relation to measurement of the sample and the luminescence attenuation thus caused can be measured as described above. The toxicity signal produced by the known substance may then serve as a reference signal for signals produced by unknown substances and a statement may be made as to the factor by which the sizes (expressed as peak height or peak area) of the signal produced by the unknown substance and the signal produced by a known quantity of the comparison compound differ from one another.

Vibrio harveyi ATCC 14126 and Xenorhabdus luminescens ATCC29999 have proven to be particularly suitable strains of bacteria for HPLC applications. Surprisingly neither of these strains display any significant reduction in luminescence even when the eluent has a composition of as high as 25% methanol in water. Substances which are toxic to bacteria are still nevertheless detected by their reduction in luminescence. Thus the scope of application of HPLC for the detection of toxicity can be extensively broadened compared with the use of water alone as the eluent.

What is claimed is:

1. An analytic process for testing for the presence of toxic components in a mixture of components, said process comprising separating said mixture into separate components by chromatography in a chromatographic system, directly contacting a separated component with a strain of luminescent microorganism within the chromatographic system itself, and determining a reduction in the luminescence of said microorganisms, said reduction in the luminescence of said microorganisms indicating that said separated component is toxic.

2. A process according to claim 1, wherein the components are separated by thin layer chromatography.

3. A process according to claim 2, wherein the components are separated on a thin layer chromatography plate, the separated components are contacted with a strain of luminescent microorganisms by wetting said plate with a suspension of said luminescent microorganisms, and a local reduction of bioluminescence is assigned to separated components individually and is measured.

4. A process according to claim 3, wherein the thin layer chromatography plate is contacted with a photographic film and the bioluminescence assigned to the separated components is evaluated on the exposed film either visually or by densitometry.

5. A process according to claim 3, wherein said suspension is an aqueous suspension consisting of the luminescent microorganisms, water and sodium chloride.

6. A process according to claim 1, wherein the components are separated by column liquid chromatography.

7. A process according to claim 6, wherein the components are separated on a column and separately eluted therefrom, the separated components are contacted with a strain of luminescent microorganisms by mixing the separate eluates from said column with a suspension of said luminescent microorganisms, and the bioluminescence of said mixture is measured.

8. A process according to claim 7, wherein the bioluminescence of said mixture is measured by a throughflow photometer.

9. A process according to claim 7, wherein said suspension is an aqueous suspension consisting of the luminescent microorganisms, water and sodium chloride.

10. A process according to claim 7, wherein said luminescent microorganisms are selected from the group consisting of Vibrio harveyi ATCC 14126 and Xenorhabdus ATCC 29999.

* * * * *